United States Patent [19]

Balkovec et al.

[11] Patent Number: 5,646,245

[45] Date of Patent: Jul. 8, 1997

[54] PROCESS FOR PREPARING SIDE CHAIN DERIVATIVES OF CYCLOHEXAPEPTIDYL LIPOPEPTIDES

[76] Inventors: James M. Balkovec, 210 Clinton Ave., North Plainfield, N.J. 07063; Frances A. Bouffard, 1521 Cooper Rd., Scotch Plains, N.J. 07076; James F. Dropinski, 307 Hampshire Ct., Piscataway, N.J. 08854; Akinlolu A. Adefarati, 180C Overlook Ct., Woodbridge, N.J. 07095; Jan S. Tkacz, 620 South Randolphville Rd., Piscataway, N.J. 08854

[21] Appl. No.: 648,741

[22] Filed: May 16, 1996

Related U.S. Application Data

[63] Continuation of Ser. No. 295,176, Aug. 23, 1994, abandoned.

[51] Int. Cl.[6] .............................. C07K 7/64; A61K 38/12
[52] U.S. Cl. ............... 530/317; 930/270; 930/DIG. 546; 930/DIG. 548
[58] Field of Search ................... 530/317; 514/9, 514/11; 930/270, DIG. 548, DIG. 546

[56] References Cited

U.S. PATENT DOCUMENTS

| | | | |
|---|---|---|---|
| 5,159,059 | 10/1992 | Balkovec et al. | 530/317 |
| 5,166,135 | 11/1992 | Schmatz et al. | 530/317 |
| 5,194,377 | 3/1993 | Schwartz et al. | 530/317 |
| 5,202,309 | 4/1993 | Schwartz et al. | 530/317 |
| 5,310,873 | 5/1994 | Schmatz et al. | 530/317 |
| 5,378,804 | 1/1995 | Balkovec et al. | 530/317 |
| 5,516,756 | 5/1996 | Balkovec et al. | 514/11 |
| 5,552,521 | 9/1996 | Belyk et al. | 530/317 |

FOREIGN PATENT DOCUMENTS

| | | |
|---|---|---|
| 851310 | 8/1977 | Belgium . |
| 859067 | 3/1978 | Belgium . |
| 459564 | 12/1991 | European Pat. Off. . |
| 486011 | 5/1992 | European Pat. Off. . |
| 539088 | 4/1993 | European Pat. Off. . |

OTHER PUBLICATIONS

Schwartz, et al. J. Antibiotics, 45(12), pp. 1853–1866 (1992).

Bouffard, et al., J Med. Chem., 37(2) pp. 222–225 (1994).

*Primary Examiner*—Harold E. Schain
*Attorney, Agent, or Firm*—Elliott Korsen; Mark R. Daniel

[57] ABSTRACT

An improved process for the preparation of side chain derivatives of cyclohexapeptidyl lipopeptides represented by the formula

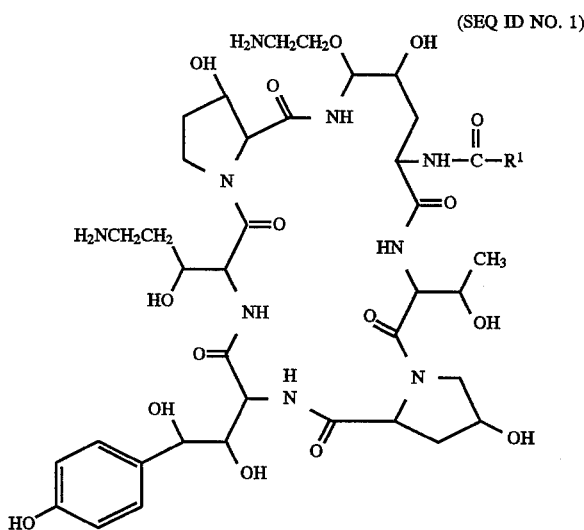

(SEQ ID NO. 1)

wherein $R^1$ is fully defined, is disclosed.

1 Claim, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Xaa  Thr  Xaa  Xaa  Xaa  Xaa
    1                       5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

Xaa  Thr  Xaa  Xaa  Xaa  Xaa
    1                       5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

```
Xaa Thr Xaa Xaa Xaa Xaa
1               5
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:4:

```
Xaa Thr Xaa Xaa Xaa Xaa
1               5
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:5:

```
Xaa Thr Xaa Xaa Xaa Xaa
1               5
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:6:

```
Xaa Thr Xaa Xaa Xaa Xaa
1               5
```

PROCESS FOR PREPARING SIDE CHAIN DERIVATIVES OF CYCLOHEXAPEPTIDYL LIPOPEPTIDES

This is a continuation of application Ser. No. 08/295,176 filed Aug. 23, 1994, now abandoned.

BACKGROUND OF THE INVENTION

The present invention is directed to an improved process for the preparation of side chain derivatives of certain amine-containing cyclohexapeptidyl lipopeptides. These side chains are attached at the α-amino-nitrogen of the 1-[hydroxyornithine] residue of the cyclohexapeptide which can be represented by the formula (SEQ ID NO. 1)

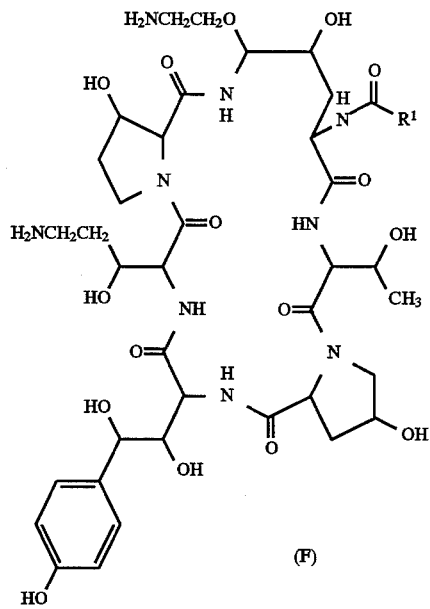

(F)

wherein $R^1$ is hereinafter fully defined.

Previously, side chain derivatives of these amine-containing lipopeptides have been prepared via a deacylation-reacylation sequence followed by the chemical conversion of the 3-hydroxyglutamine residue to a 3-hydroxyornithine residue. This scheme, however, provides very low yields and requires optimization for each derivative.

It is therefore an object of this invention to provide an improved process for the preparation of the side chain derivatives in high yield.

DETAILED DESCRIPTION OF THE INVENTION

According to the present invention, it has been discovered that certain amine-containing cyclohexapeptides represented by the formula (SEQ ID NO. 1)

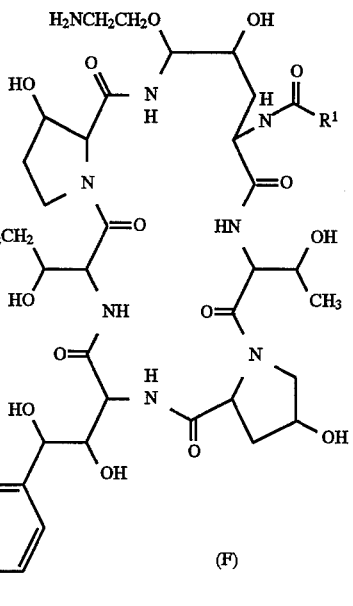

(F)

wherein $R^1$ is $C_9$–$C_{21}$ alkyl, $C_9$–$C_{21}$ alkenyl, $C_1$–$C_{10}$ alkoxyphenyl, $C_1$–$C_{10}$ alkoxynaphthyl, or

wherein $R^a$ is $C_1$–$C_{10}$ alkyl; or $(CH_2)_q NR^b R^c$ wherein $R^b$ and $R^c$ are independently H, $C_1$–$C_{10}$ alkyl or $R^b$ and $R^c$ taken together with the N atom are

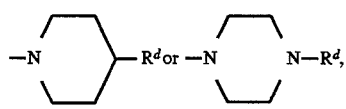

wherein $R^d$ is $C_1$–$C_{16}$ alkyl, phenyl or benzyl;

p is 1 or 2, and q is 2, 3 or 4; may be obtained in good and more reproducible yields and in good purity by the novel process as set forth below.

The process comprises (a) sequentially reacting a cyclohexapeptide of the formula

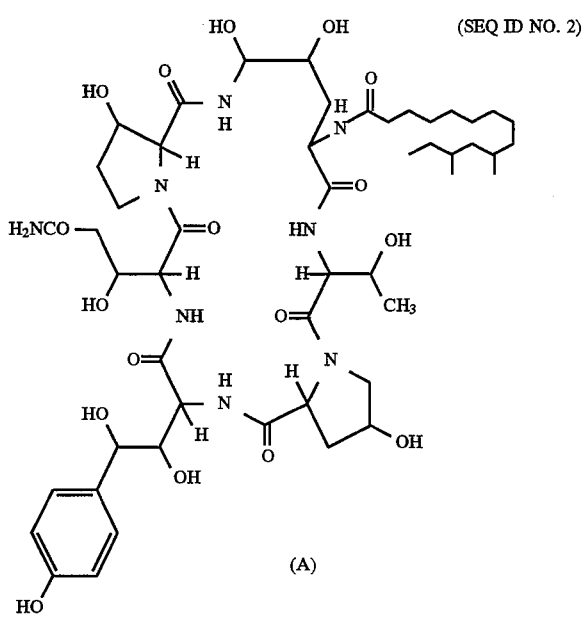

(A) (SEQ ID NO. 2)

with a dehydrating agent, a reducing agent and an etherification agent to obtain an aminoalkyl ether derivative of the formula

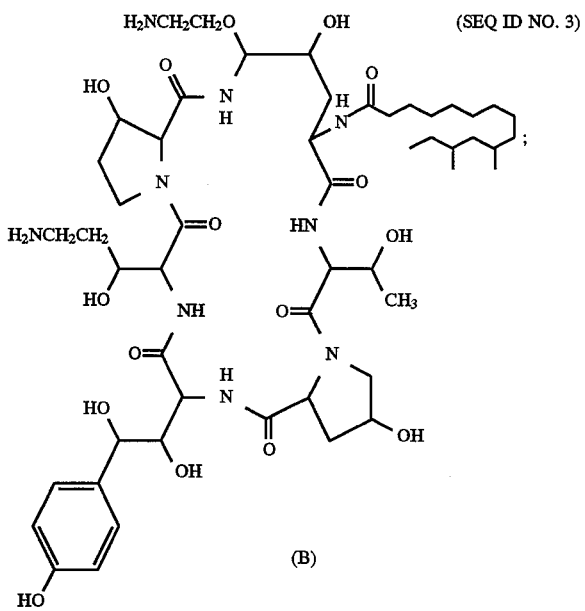

(B) (SEQ ID NO. 3)

(b) deacylating the ether derivative to obtain a compound of the formula

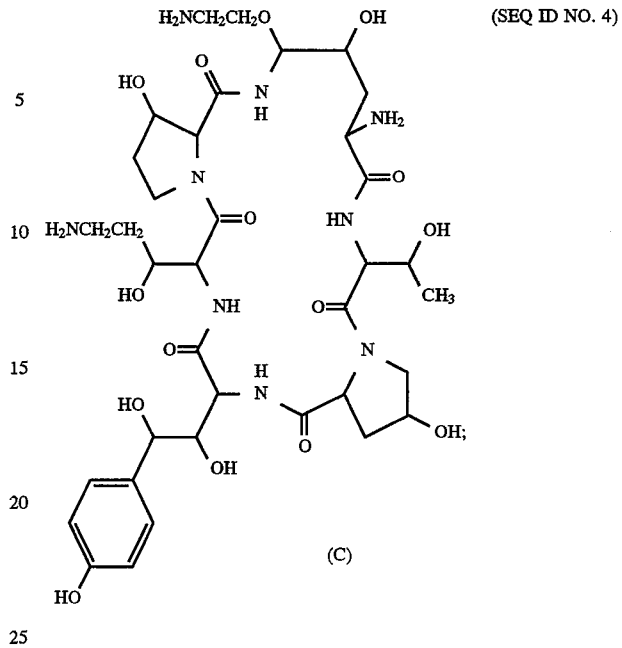

(C) (SEQ ID NO. 4)

(c) preferentially protecting two of the three amino groups by reaction with a suitable protecting group to afford a compound of the formula

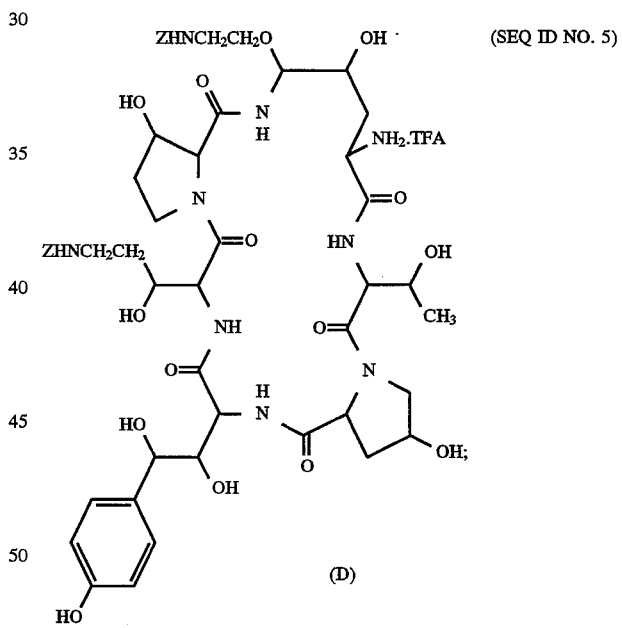

(D) (SEQ ID NO. 5)

(d) reacylating the unprotected amino group by reaction with a suitable activated ester to afford a compound of the formula

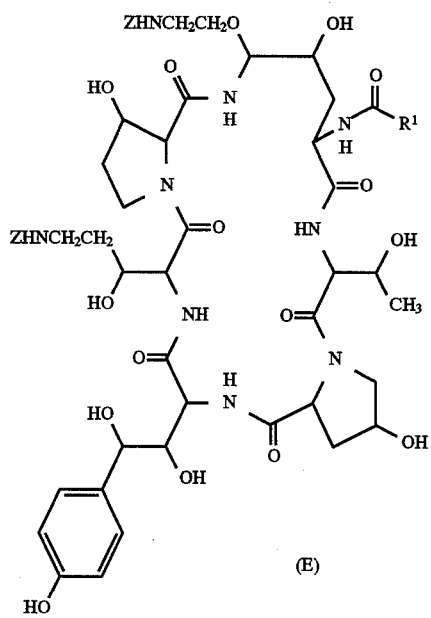

(E) (SEQ ID NO. 6)

and (e) deprotecting the protected amino groups to afford a compound of the formula

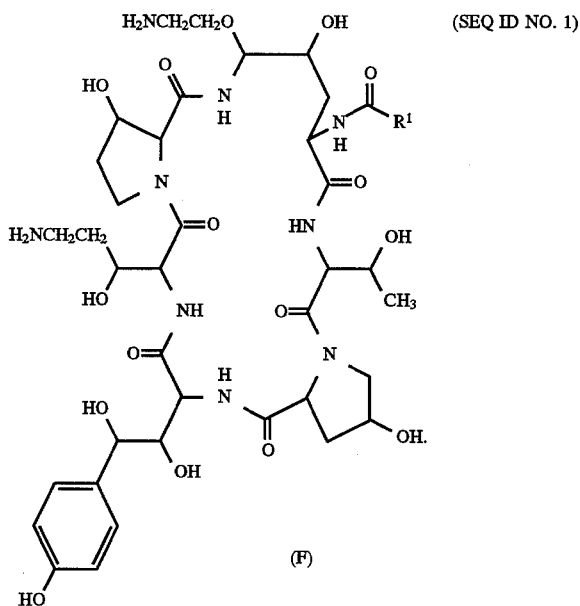

(F) (SEQ ID NO. 1)

The process of this invention is illustrated in greater detail in Scheme I below.

The invention is described herein using the terms defined below unless otherwise specified.

The term "alkyl" refers to a monovalent alkane (hydrocarbon) derived radical containing from 1 to 30 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to three substituent groups at any available point of attachment. When the alkyl group is said to be substituted with an alkyl group, this is used interchangeably with "branched alkyl group". When the alkyl group may be at any available point of attachment. The alkyl portion of "alkoxy" is also defined as above.

Cycloalkyl is a specie of alkyl containing from 3 to 15 carbon atoms, without alternating or resonating double bonds between carbon atoms. It may contain from 1 to 4 rings which are fused. The preferred cycloalkyl groups are cyclopentyl and cyclohexyl.

Alkoxy refers to $C_1$–$C_4$ alkyl-O—, with the alkyl group optionally substituted.

SCHEME I
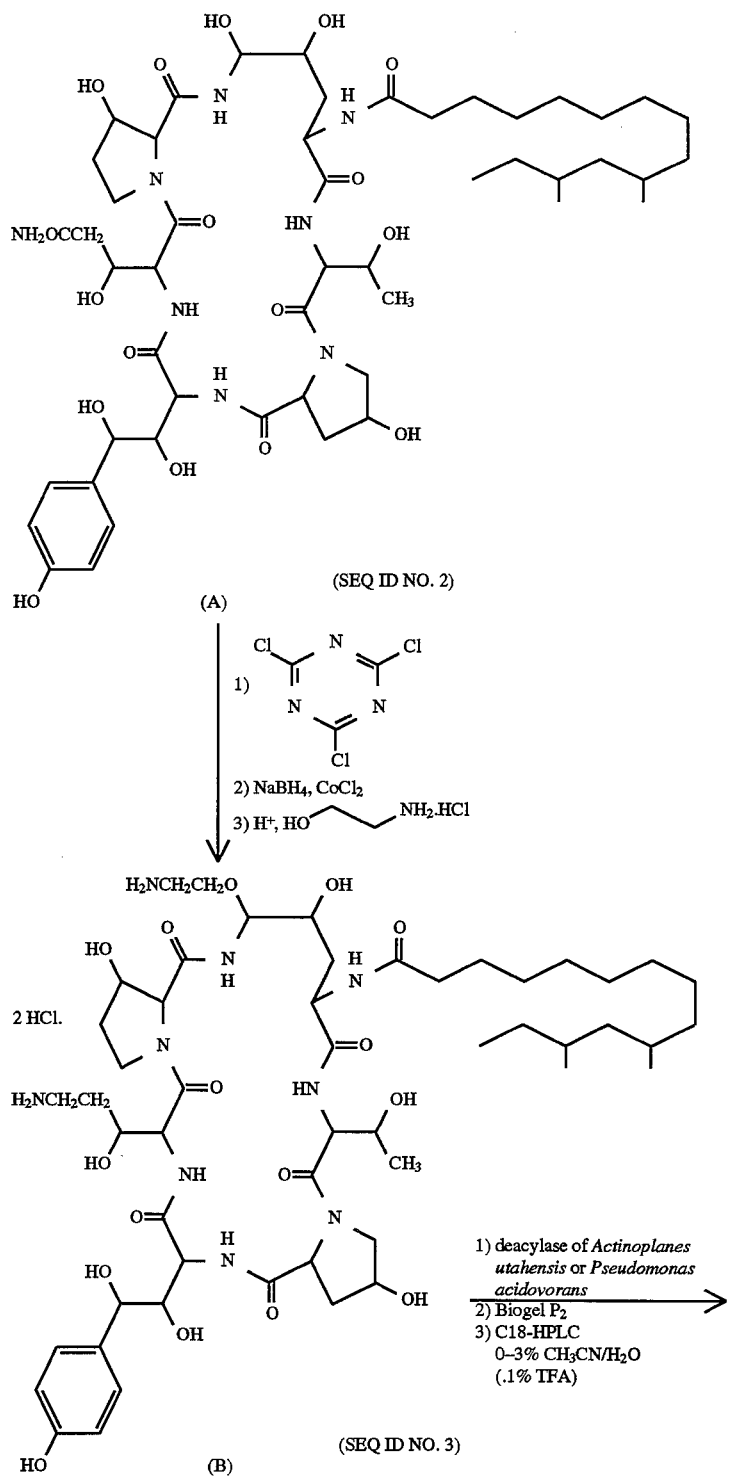
(A) (SEQ ID NO. 2)
1) [cyanuric chloride]
2) NaBH₄, CoCl₂
3) H⁺, HOCH₂CH₂NH₂·HCl
(B) (SEQ ID NO. 3)
1) deacylase of *Actinoplanes utahensis* or *Pseudomonas acidovorans*
2) Biogel P₂
3) C18-HPLC 0–3% CH₃CN/H₂O (.1% TFA)

-continued
SCHEME I
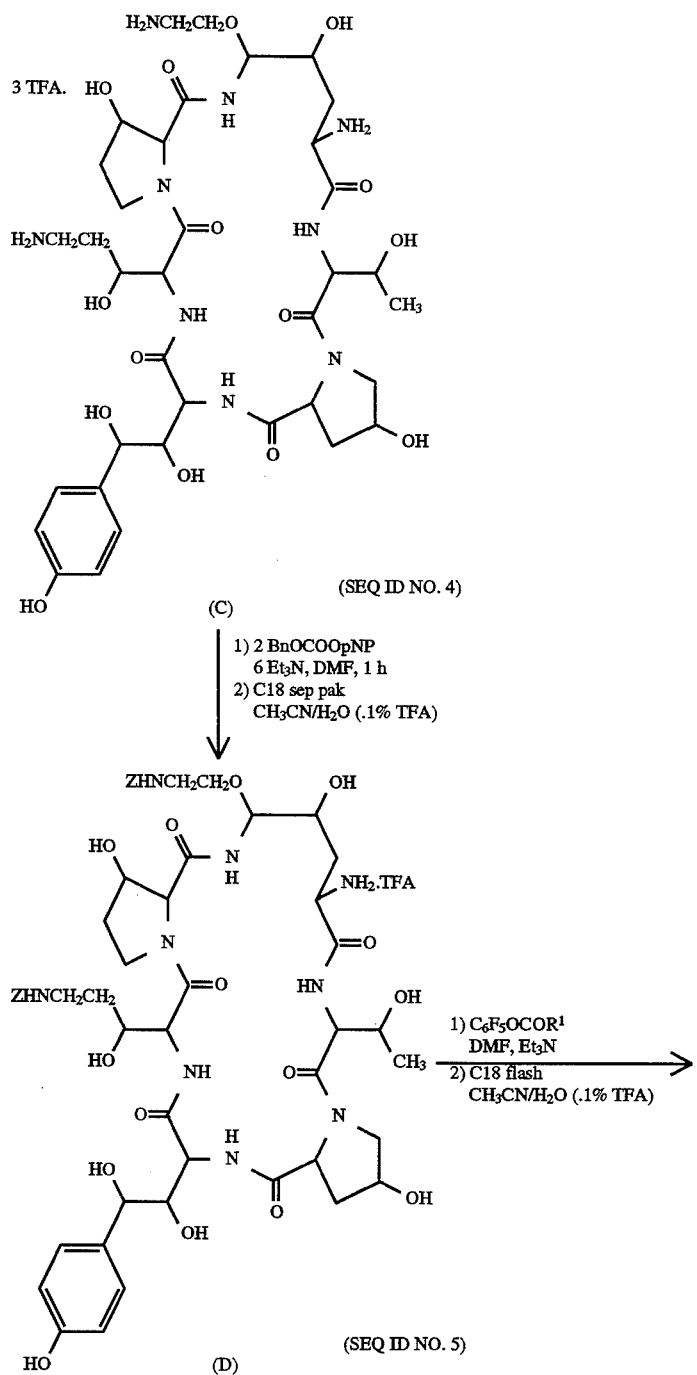
(C) (SEQ ID NO. 4)
1) 2 BnOCOOpNP
   6 Et₃N, DMF, 1 h
2) C18 sep pak
   CH₃CN/H₂O (.1% TFA)
1) C₆F₅OCOR¹
   DMF, Et₃N
2) C18 flash
   CH₃CN/H₂O (.1% TFA)
(D) (SEQ ID NO. 5)

-continued
SCHEME I

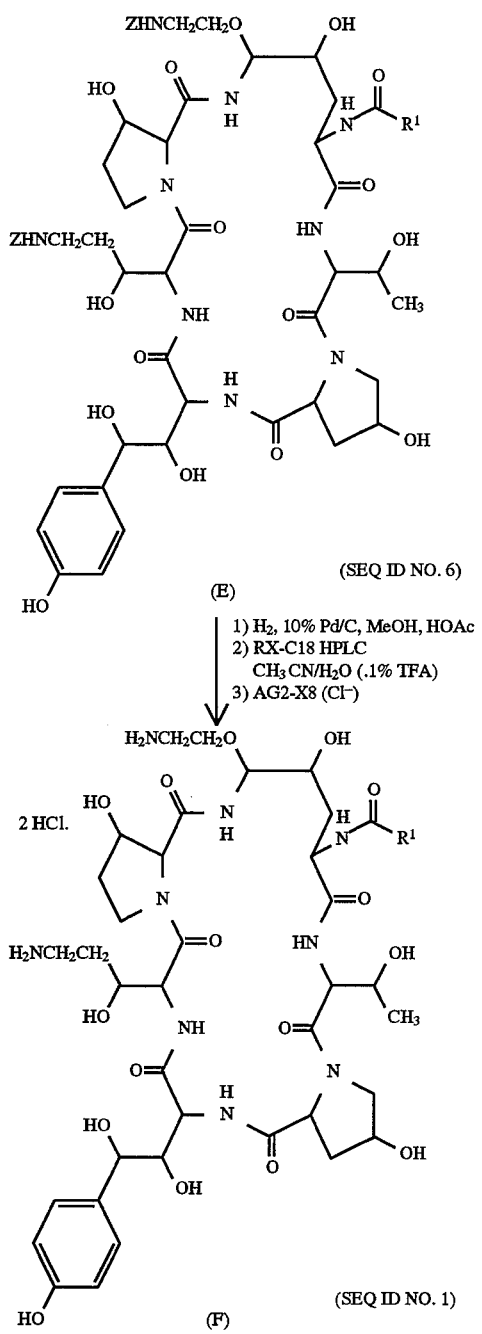

(SEQ ID NO. 6) (E)

1) H₂, 10% Pd/C, MeOH, HOAc
2) RX-C18 HPLC
   CH₃CN/H₂O (.1% TFA)
3) AG2-X8 (Cl⁻)

(SEQ ID NO. 1) (F)

Compound A, which is described in U.S. Pat. No. 5,202,309 and whose preparation is disclosed in U.S. Pat. No. 5,194,377 is reacted first with a dehydrating agent, then reduced with a reducing agent, and subsequently etherified to afford Compound B.

The dehydration of the carboxamide group is carried out preferentially with cyanuric chloride. Other reagents which may be employed in place of cyanuric chloride are anhydrides such as acetic anhydride, trifluoroacetic anhydride and phosphorus pentoxide; acid chlorides such as oxalyl chloride, phosphorus oxychloride, thionyl chloride, p-toluenesulfonyl chloride and chlorosulfonyl isocyanate; phosphonium reagents such as phosphorus pentachloride, triphenylphosphine/carbon tetrachloride, triphenylphospho-nium ditriflate and triphenylphosphonium dichloride; carbodiimides such as dicyclohexylcarbodiimide; other dehydrating agents such as aluminum chloride, titanium tetrachloride, ethyl(carboxysulfamoyl) triethylammonium hydroxide or inner salt.

The reaction is carried out in a solvent such as dimethylformamide (DMF). Other solvents which may be employed include pyridine, collidine and other weakly basic solvents.

The relative amounts of Compound A and the dehydrating agent vary but generally the dehydrating agent is used in excess. From about 1.5 to 15 equivalents of the dehydrating agent are employed.

The reducing agent is employed to reduce the resulting nitrile intermediate formed. This reduction may be carried out employing either chemical or catalytic reduction. When chemical reduction is employed, hydride or hydride combinations have been found useful.

Sodium borohydride with cobaltous chloride in alcoholic solvent has been found to be particularly useful. When this combination of reagents is used, from about 5 to 50 molar equivalents of sodium borohydride and from about 2 to 10 molar equivalents of cobaltous chloride are used for each molar amount of the nitrile.

Other hydride reducing agents such as Raney nickel, sodium cyanoborohydride, aluminum hydride, diborane, diisobutyl aluminum hydride and the like also may be used. Frequently these reducing agents are used in combination with a Lewis acid such as cobaltous chloride or aluminum chloride as in the present combination of sodium borohydride and cobaltous chloride.

Catalytic hydrogenation also may be carried out over a variety of catalysts including palladium on carbon, platinum oxide, or rhodium on alumina. Low pressure catalytic reduction over Pd/C catalyst is especially preferred.

Typical solvents depending on the reagent include alcohols, especially methanol and ethanol, dimethylformamide, pyridine, tetrahydrofuran or other ethers.

Following these steps, the OH group is reacted with an amino alcohol as a salt to obtain Compound B.

Compound B can be deacylated by employing a microbial deacylating agent such as *Actinoplanes utahensis* deacylase or *Pseudomonas acidovorans* deacylase to afford Compound C. Compound C of the formula

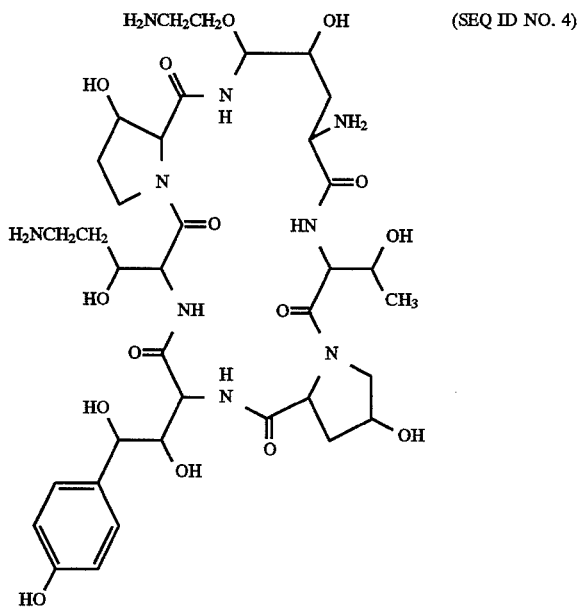

(SEQ ID NO. 4)

is a novel intermediate which is essential to the process of this invention. Compound C can be further purified by treatment with Biogel P2 and further through HPLC employing reverse phase C18 column chromatography.

Compound C, which contains three reactive amine groups, can be selectively protected by reaction with an appropriate protecting group. Conventional protecting groups are employed with the carbobenzyloxy group (CBz) preferred. Other groups include fluorenylmethyl carbamates (Fmoc) removable under basic conditions and t-butyl carbamates (t-BOC) removable under acidic conditions. Any group that selectively protects the three reactive amines can be used.

A solvent is employed in carrying out the protection reaction. Suitable solvents include triethylamine, DMF, acetonitrile, pyridine or n-methylpyrrolidinone. This reaction typically takes place at a temperature of about −20° to 25° C. for about 0.5 to 12 hours.

Compound D can be isolated pure by flash chromatography using $CH_3CN/H_2O$ containing 0.1% trifluoroacetic acid (TFA).

Compound D as the TFA salt of the disubstituted ornithine residue can then be reacylated at the unprotected amine group with any of the defined $R^1$ groups by reaction with from one to ten equivalents of an activated ester to form Compound E. An activated ester is one which is known to one skilled in the art to acylate an amine group. Such esters include phenyl, p-nitrophenyl, pentafluorophenyl, pentachlorophenyl, N-hydroxysuccinimide, 3,5-dichlorophenyl, thiophenyl, 2-thiopyridyl and the like. Acylating agents are not limited to activated esters. Other types of reactive acylating agents which may be employed include acid chlorides, acid anhydrides and orthoesters.

The reacylation typically takes place in a suitable solvent such as DMF, N-methylpyrrolidinone, tetrahydrofuran, pyridine, triethylamine or a combination of such solvents at a temperature of about 25° to 60° C. for about 1 to 72 hours. The product is further purified by flash chromatography or HPLC using a $C_8$ or $C_{18}$ reverse phase column. The two protected amines are not attacked by the activated ester with the reaction occurring exclusively at the α-amino-nitrogen of the disubstituted ornithine residue.

Compound D need not necessarily be isolated. Alternatively, the $R^1$ side chain group may be introduced to give Compound E directly in the reaction in which Compound D was formed. The acylation may be accomplished by adding an activated ester directly to the reaction mixture containing Compound D at a temperature of about 25° to 60° C. and stirring from about 1 to 72 hours. The acylation conditions and purification of Compound E have been described above and are applicable whether Compound D is first isolated or is acylated directly in the reaction vessel after formation.

Compound E subsequently undergoes deprotection to remove the protecting groups. The carbobenzyloxy group (CBz) may be removed by low pressure hydrogenation in the presence of 10% Pd/C. The hydrogenation is monitored by analytical HPLC with an acetonitrile/water solvent system containing 0.1% TFA. When substantial completion of the reaction has occurred, the reaction mixture is filtered to remove the catalyst, the filtrate concentrated in vacuo or lyophilized and the product purified using preparative HPLC. Other protecting groups such as Fmoc or t-BOC may be removed by base or acid treatment, respectively, or other methods known to those skilled in the art.

The compounds produced by the process of the invention are useful as an antibiotic, especially as an antifungal or antiprotozoal agent. As antifungal agents they are useful for the control of both filamentous fungi and yeasts. They are especially adaptable to be employed for the treatment of mycotic infections in mammals, especially those caused by Candida species such as *C. albicans*, *C. tropicalis* and *C. pseudotropicalis*, Cryptococcus species such as *C. neoformans* and Aspergillus species such as *A. fumigatus*, *A. flavus*, *A. niger*. They are also useful for the treatment and/or prevention of *Pneumocystis carinii* pneumonia to which immune compromised patients are especially susceptible.

The following examples illustrate the invention but are not construed as limiting the invention described herein.

EXAMPLE 1

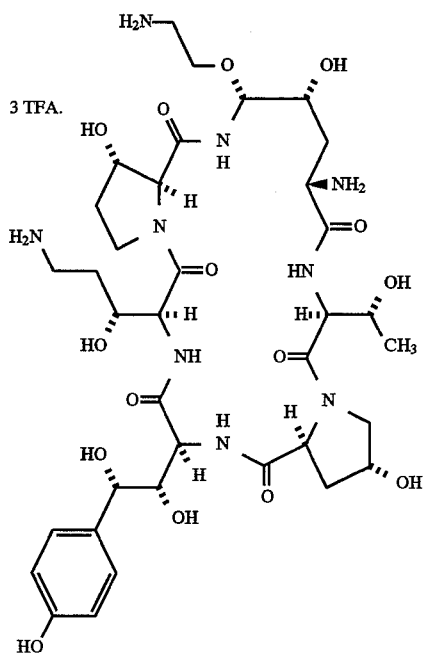

(SEQ ID NO. 4)

EXAMPLE 1

A. Preparation of the Deacylating Enzyme

*P. acidovorans* ATCC 53942, maintained on Luria-Bertani medium agar slants was used to produce the deacylation enzyme.

A seed culture was prepared by inoculating a 50-mL portion of Luria-Bertani medium in a 250 mL flask with a loopful of the bacterium and the culture was incubated for about 24 hours at 27° C. with constant shaking. Cells for the deacylation were grown by inoculating 15 liters of Luria-Bertani medium in a stirred fermentor with 30 mL of the seed culture and incubating with agitation of 400 rpm and aeration at 7.5 liters/min. at 28° C. for 20 to 24 hours. The cells were washed with 50 mM potassium phosphate buffer, pH 7.5 and resuspended in about 4 liters of the same buffer. The suspension was equilibrated to 37° C. to obtain the deacylating enzyme.

B. Deacylation of Compound B

Two liters of such suspension was used to deacylate 3.5 g of Compound B. 3.5 g of Compound B was dissolved in about 900 mL of distilled water and added slowly over a 1 hour period to 2 liters of the suspension of *P. acidovorans* cells maintained at 37° C. and stirred at about 300 rpm without aeration. After 24 hours, the deacylation mixture was cleared of *P. acidovorans* cells by centrifugation and 1.8 liters of supernatant was collected.

C. Isolation of Compound C

Purification of Compound C began by the addition of 45 mL of 10% aqueous trifluoroacetic acid to 900 mL of the supernatant obtained above. The solution was filtered to remove particulate matter then purified by reverse phase chromatography (DELTA PAK C-18, 45×300 mm radial-pack column packed in 100% water containing 0.1% trifluoroacetic acid, 50 mL/min, λ=230 nm). The appropriate fractions, as determined by analytical HPLC (ZORBAX Rx-C18, 2.5% aqueous acetonitrile/0.1% trifluoroacetic acid, 1 mL/min, λ=210 nm), were pooled and lyophilized. An identical purification on the remaining 900 mL of supernatant gave material that was combined with material from the first purification to give a total of 1.3 g of deacylated lipopeptide. FAB-MS (M+H) m/z 856; $^1$H NMR (400 MHz, CD$_3$OD) δ7.12 (d), 6.77 (d), 5.23 (d), 5.02 (d), 3.17 (m), 3.05 (t), 1.29 (d).

EXAMPLE 2

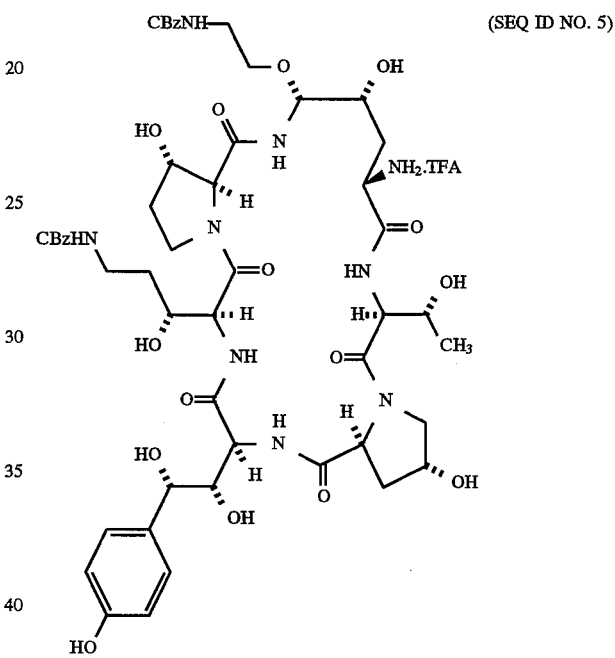

(SEQ ID NO. 5)

To a solution of the nucleus (33.1 mg, 0.0276 mmol) from Example 1 and benzyl 4-nitrophenylcarbonate (15.1 mg, 0.0553 mmol) in anhydrous N,N-dimethylformamide was added triethylamine (23.1 μl, 0.166 mmol). The reaction mixture was stirred for a period of 1 hour and then diluted with H$_2$O (4 ml). C18-Flash chromatography of the resultant aqueous solution eluting with 10–35% CH$_3$CN/H$_2$O (0.1% CF$_3$COOH) in 5% step-gradients was followed by lyophilization of the product-containing fractions as determined by analytical HPLC (Zorbax RX-C18, 25% CH$_3$CN/H$_2$O (0.1% CF$_3$COOH) at 1.5 ml/min, uv detection at 277 nm) to give the selectively protected nucleus: FAB-MS (Li) m/z 1130.1, 1124.1; $^1$H NMR (400 MHz, CD$_3$OD) δ1.28 (d), 3.21 (t), 3.51 (m), 5.08 (s), 6.76 (d), 7.12 (d), 7.31 (m).

EXAMPLE 3

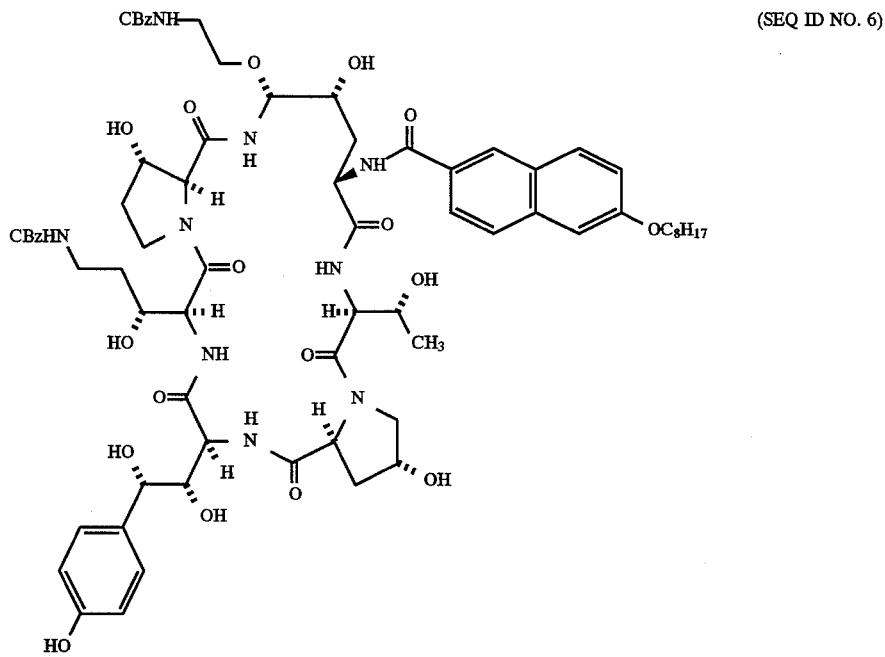

(SEQ ID NO. 6)

Part A: Preparation of Pentafluorophenyl 6-Octyloxy-2-naphthoate

To a suspension of 6-octyloxy-2-naphthoic acid (3.15 g, 10.5 mmol) and dicyclohexylcarbodiimide in ethyl acetate (25 ml) at 0° C. was added pentafluorophenol (2.12 g, 11.5 mmol). The mixture was stirred at 25° C. for a period of 18 h. The precipitate was removed by filtration. The filtrate was washed with water (2×150 ml) and brine and dried with magnesium sulfate. Removal of the ethyl acetate in vacuo gave 5.4 g of pentafluorphenyl 6-octyloxy-2-naphthoate as a solid: $^1$H NMR (400 MHz, CD$_3$OD) δ0.88 (t, 3H, J=6.9 Hz), 4.10 (t, 2H, J=6.6 Hz), 7.16 (d, 1H), 7.21 (d, 1H), 7.80 (d, 1H), 7.87 (d, 1H), 8.08 (dd, 1H), 8.69 (d, 1H).

Part B: Preparation of the Coupled Nucleus

Pentafluorophenyl 6-octyloxy-2-naphthoate prepared as described in Part A (20.5 mg, 0.044 mmol) was added to a solution of the protected nucleus from Example 2 (45 mg, 0.040 mmol) in anhydrous N,N-dimethylformamide (2.1 ml). The resulting solution was stirred at room temperature for a period of 22 h. Dilution with water (8 ml) produced a heterogeneous mixture. C18-Flash chromatography of the mixture eluting with 30–100% CH$_3$CN/H$_2$O in 10% step gradients followed by lyophilization of the product-containing fractions as determined by analytical HPLC (Zorbax RX-C18, 70% CH$_3$CN/H$_2$O (0.1% CF$_3$COOH) at 1.5 ml/min, uv detection at 210 nm) gave 19 mg of the above compound as an amorphous solid: $^1$H NMR (400 MHz, CD$_3$OD) δ0.90 (t, 3H, J=7.0 Hz), 1.21 (d, 3H, J=5.8 Hz), 1.53 (m, 2H), 1.66 (m, 1H), 2.43 (dd, 1H, J=7.0 and 13.2 Hz), 3.39 (m, 1H), 3.51 (m, 1H), 3.60 (m, 1H), 3.81 (m, 3H), 3.97 (dd, 1H, J=3.0 and 11.2 Hz), 4.10 (t, 2H, J=6.4 Hz), 4.17 (m, 1H), 4.56 (m, 3H), 5.30 (dd, 1H, J=1.6 and 9.3 Hz), 6.75 (d, 2H, J=8.6 Hz), 7.23 (m), 7.67 (m), 7.86 (dd, 1H, J=1.7 and 8.7 Hz), 8.33 (s, 1H), 8.38 (d, 1H, J=8.9 Hz); FAB-MS (Li) m/z 1412.0.

EXAMPLE 4

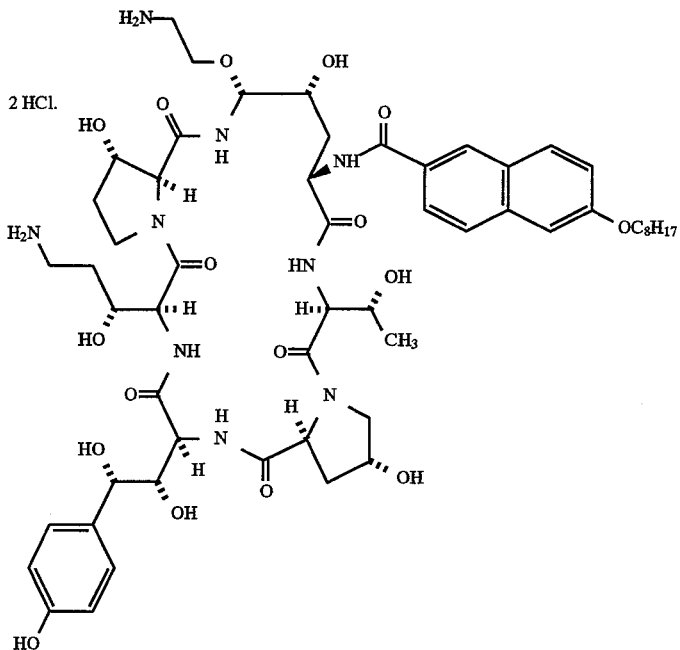

(SEQ ID NO. 1)

A solution of the di-CBZ coupled nucleus from Example 3 (19 mg, 0.0135 mmol) in methanol (4 ml) and glacial acetic acid (0.5 ml) was hydrogenated under balloon pressure in the presence of 10% Pd/C (20 mg) for a period of 1 h. The reaction mixture was filtered through a bed of diatomaceous earth to remove the catalyst, rinsing with MeOH. The filtrate was concentrated in vacuo. C18-Flash chromatography of the residue eluting with 10–45% $CH_3CN/H_2O$ (0.1% $CF_3COOH$) in 5% step gradients followed by lyophilization of the product-containing fractions as determined by analytical HPLC (Zorbax RX-C18, 70% $CH_3CN/H_2O$ (0.1% $CF_3COOH$) at 1.5 ml/min, uv detection at 210 nm) gave 9.9 mg of impure product. Rechromatography of this material (Zorbax RX-C18, 21.2 mm×25 cm, 10–40% $CH_3CN/H_2O$ (0.1% $CF_3COOH$), 5% step gradients, uv detection at 277 nm) gave 6.3 mg of the di-trifluoroacetate salt. Conversion to the dihydrochloride form on a strong anion exchange column ($Cl^-$) eluting with water gave, after lyophilization, 5.5 mg of the product shown above as an amorphous solid: $^1H$ NMR (400 MHz, $CD_3OD$) δ0.91 (t, 3H, J=6.9 Hz), 1.22 (d, 3H, J=6.1 Hz), 1.53 (m, 2H), 2.45 (dd, 1H, J=6.9 and 13.1 Hz), 3.09 (t, 2H, J=5.0), 3.16 (m, 2H), 3.65 (m, 1H), 4.00 (dd, 1H, J=3.1 and 6.5 Hz), 4.12 (t, 2H, J=6.5 Hz), 5.03 (d, 1H, J=3.2 Hz), 5.28 (d, 1H, J=2.1 Hz), 6.75 (d, 2H, J=8.6 Hz), 7.12 (d, 2H, J=8.6 Hz), 7.21 (m, 1H), 7.28 (d, 1H, J=2.2 Hz), 7.84 (m, 3H), 8.36 (brs, 1H); FAB-MS (Li) m/z 1144.6, 1083.4.

EXAMPLE 5

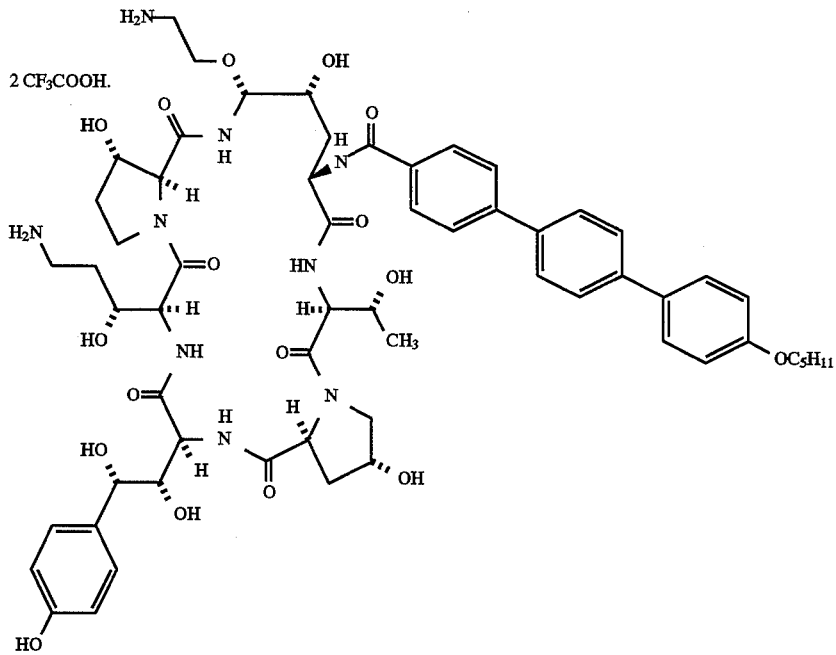

(SEQ ID NO. 1)

Part A: 4-(n-Pentoxyphenyl)-4'-pentafluorophenoxycarbonylbiphenyl

Step 1: 4-(4-n-Pentoxyphenyl)phenylboronic acid

To a stirred suspension of 4-(4-n-pentoxyphenyl) bromobenzene (1.0 g, 3.13 mmol) in anhydrous tetrahydrofuran (20 ml) at −78° C. under a nitrogen atmosphere was added n-butyllithium in hexanes (2.5M, 1.32 ml, 3.30 mmol). After a period of 15 rain, triisopropylborate (760 µl, 3.30 mmol) was added. Stirring at −78° C. was continued for 15 min and then at 25° C. for 40 min. The mixture was acidified with 0.5N HCl (20 mL) and then partitioned between ether (50 ml) and water (40 ml). The organic phase was washed with water (3×) and brine and dried with magnesium sulfate. The solvent was removed in vacuo to give 4-(4-n-pentoxyphenyl)phenylboronic acid (750 mg) as a solid: $^1$H NMR (400 MHz, DMSO-d$_6$) δ0.89 (t, 3H, J=7.2 Hz), 1.38 (m, 4H), 1.72 (m, 2H), 3.99 (t, 2H, 1–6.5Hz), 6.99 (d, 2H, J=8.8 Hz), 7.57 (d, 2H, J=8.2 Hz), 7.60 (d, 2H, J=8.8 Hz), 7.83 (d, 2H, J=8.2 Hz).

Step 2: 4-(4-n-Pentoxyphenyl)bromobenzene

To a stirred solution of 4-(4-bromophenyl)phenol (25.5 g, 0.102 mol) in 400 mL of dimethylsulfoxide was added 2.5N NaOH (40.9 ml, 0.102 mol) followed by n-pentyl bromide (12.7 mL, 0.102 mol). The resulting mixture was heated at 70° C. for a period of 18 h. After cooling, the solution was partitioned between ethyl acetate (1000 ml) and water (500 ml). The organic phase was washed with water (3×) and brine and dried with magnesium sulfate. The solvent was removed in vacuo to give 30.9 g of 4-(4-n-pentoxyphenyl) -bromobenzene: $^1$H NMR (400 MHz, DMSO-d$_6$) δ0.93 (t, 3H, J=7.2 Hz), 1.41 (m, 4H), 1.79 (m, 2H), 3.97 (t, 2H, J=6.6 Hz), 6.94 (d, 2H, J=8.8 Hz), 7.39 (d, 2H, J=8.6 Hz), 7.45 (d, 2H, J=8.8 Hz), 7.51 (d, 2H, J=8.6 Hz).

Step 3: 4-(n-Pentoxyphenyl)-4'-carboxybiphenyl

To a stirred mixture of 4-(4-n-pentoxyphenyl) phenylboronic acid (1.0 g, 3.52 mmol) and 4-iodobenzoic acid (874 mg, 3.52 mmol) in ethanol (11 ml) and toluene (30 ml) was added an aqueous solution of sodium carbonate (2M, 5.3 ml, 10.6 mmol) followed by tetrakis (triphenylphosphine)palladium (204 mg, 5 mol %). The reaction mixture was heated at 100° C. under a nitrogen atmosphere for a period of 18 h. The cooled mixture was acidified to pH 3 (1N HCl) and partitioned between ethyl acetate and water. The organic phase was washed with water (3×) and brine, dried with magnesium sulfate, and filtered through a bed of Celite. The solvent was removed in vacuo to give crude product which was purified by flash silica gel chromatography to provide 4-(n-pentoxyphenyl)-4'-carboxybiphenyl (450 mg): $^1$H NMR (400 MHz, DMSO-d$_6$) δ0.89 (t, 3H), 1.37 (m, 4H), 1.72 (m, 2H), 3.98 (t, 2H), 7.01 (d, 2H).

Step 4: 4-(n-Pentoxyphenyl)-4'-pentafluorophenoxycarbonylbiphenyl

To a mixture of 4-(n-pentoxyphenyl)-4'-carboxybiphenyl (3.04 g, 8.43 mmol) and dicyclohexylcarbodiimide (2.28 g, 11.1 mmol) in N,N-dimethylformamide (70 ml) at 0° C. was added pentafluorophenol (4.08 g, 22.2 mmol). The mixture was stirred at 25° C. for a period of 18 h. It was then partitioned between ethyl acetate and water. The organic phase was washed with water (3×) and brine and dried with magnesium sulfate. The solvent was removed in vacuo to give 3.95 g of pentafluorophenyl ester. Trituration of the crude ester with ether and hexane provided 0.5 g of clean 4-(n-pentoxyphenyl)-4'-pentafluorophenoxycarbonylbiphenyl after suction-drying of the filter cake: $^1$H NMR (400 MHz, CDCl$_3$) δ0.93 (t, 3H), 4.01 (t, 2H), 6.98 (d, 2H) 7.56 (d, 2H), 7.67 (d, 2H), 7.70 (d, 2H), 7.79 (d, 2H), 8.26 (d, 2H).

Part B: Preparation of the Coupled Nucleus

To a stirred solution of the nucleus (103.9 mg, 0.087 mmol) from Example 1 and benzyl 4-nitrophenylcarbonate (47.4 mg, 0.173 mmol) in anhydrous N,N-dimethylformamide (3.5 ml) was added triethylamine (48.4 µl, 0.347 mmol). The reaction mixture was stirred for a period of 1 hour. 4-(n-Pentoxyphenyl)-4'-pentafluorophenoxycarbonylbiphenyl (46 mg, 0.087 mmol) prepared as described in Part A was added and stirring was continued for a period of 60 hours. Dilution with water (3.5 ml) produced a heterogeneous mixture which was partially clarified by the addition of $CH_3OH$. The product was isolated by C18 solid-phase extraction eluting initially with 40% $CH_3CN/H_2O$ and then $CH_3OH$. Concentration of the product-containing $CH_3OH$ fractions as determined by analytical HPLC (Zorbax RX-C18, 75% $CH_3CN/H_2O$ (0.1% $CF_3COOH$) at 1.5 ml/min, uv detection at 210 nm) gave 57 mg of crude di-CBZ coupled nucleus. A solution of this material in methanol (10 ml) and glacial acetic acid (4 ml) was hydrogenated under balloon pressure in the presence of 10% Pd/C (100 mg) for a period of 1.75 hours. The reaction mixture was filtered through a bed of diatomaceous earth to remove the catalyst, rinsing with MeOH. The filtrate was concentrated in vacuo. Preparative HPLC (Zorbax RX-C 18) of the residue, loaded in mobil phase containing sufficient $CH_3OH$ to fully solubilize, eluting with 40% $CH_3CN/H_2O$ (0.1% $CF_3COOH$) followed by lyophilization of the product-containing fractions as determined by analytical HPLC (Zorbax RX-C18, 70% $CH_3CN/H_2O$ (0.1% $CF_3COOH$) at 1.5 ml/min, uv detection at 210 nm) gave 30 mg of coupled, deprotected nucleus as a amorphous solid: $^1H$ NMR (400 MHz, $CD_3OD$) $\delta$0.96 (t, 3H, J=7.1 Hz), 1.22 (d, 3H, J=6.1 Hz), 1.45 (m, 4H), 2.45 (dd, 1H, J=6.8 and 12.7 Hz), 3.11 (t, 2H, 1–4.4), 3.16 (m, 2H), 3.67 (m, 1H), 4.02 (t, 2H, J=6.5 Hz), 4.11 (m, 1H), 5.03 (d, 1H, J=3.3 Hz), 5.28 (d, 1H, J=2.2 Hz), 6.76 (d, 2H, J=8.6 Hz), 7.01 (d, 2H, J=8.9 Hz), 7.12 (d, 2H, J=8.7 Hz), 7.60 (d, 2H, J=8.8 Hz), 7.70 (d, 2H, J=8.8 Hz), 7.74 (d, 2H, J=8.8 Hz), 7.80 (d, 2H, J=8.5 Hz), 7.97 (d, 2H, J =8.5 Hz); FAB-MS (Li) m/z 1204.5.

What is claimed is:
1. A compound having the formula
(SEQ ID NO. 4)
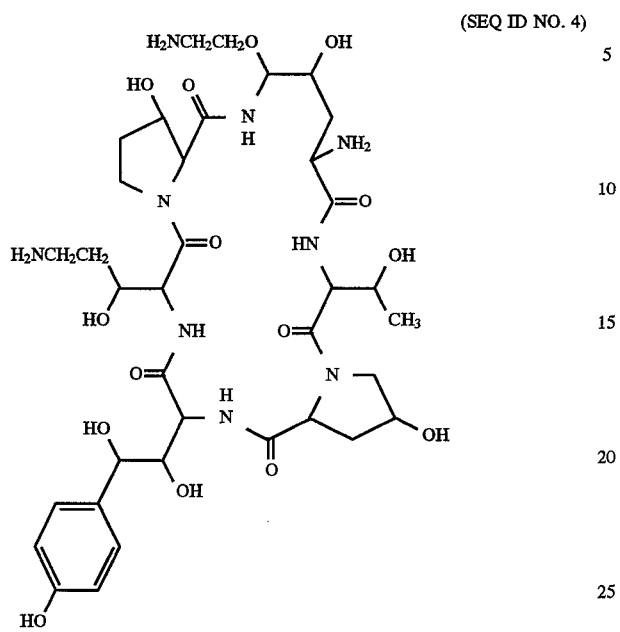
and pharmaceutically acceptable salts thereof.
* * * * *